United States Patent [19]

Kaufman et al.

[11] Patent Number: 4,721,104
[45] Date of Patent: Jan. 26, 1988

[54] FEMORAL SURFACE SHAPING APPARATUS FOR POSTERIOR-STABILIZED KNEE IMPLANTS

[75] Inventors: Michael E. Kaufman, Bartlett, Tenn.; Leo A. Whiteside, Chesterfield, Mo.

[73] Assignee: Dow Corning Wright Corporation, Arlington, Tenn.

[21] Appl. No.: 803,368

[22] Filed: Dec. 2, 1985

[51] Int. Cl.⁴ .............................................. A61F 5/04
[52] U.S. Cl. ............................ 128/92 VW; 128/92 V
[58] Field of Search .......... 128/92 V, 92 VW, 92 VP

[56] References Cited

U.S. PATENT DOCUMENTS

| | | | |
|---|---|---|---|
| 3,852,830 | 12/1974 | Marmor | 128/92 VW |
| 4,004,581 | 1/1977 | Heimke et al. | 128/92 E |
| 4,211,228 | 7/1980 | Cloutier | 128/92 VW |
| 4,284,080 | 8/1981 | Rehder | 128/305 |
| 4,328,593 | 5/1982 | Sutter et al. | 3/1.91 |
| 4,501,266 | 2/1985 | McDaniel | 128/92 VW |
| 4,522,201 | 6/1985 | Tongue | 128/92 V |
| 4,593,685 | 6/1986 | McKay et al. | 128/92 VP |

FOREIGN PATENT DOCUMENTS 2411618 4/1975 Fed. Rep. of Germany.

OTHER PUBLICATIONS

"The Howmedica® Kinematic Knee System—Howmedica Surgical Techniques", Brochure No. 3210-1 2/81 15MB, Howmedica, Inc., Rutherford, N.J., 16 pages (Feb., 1981).
"Insall/Burstein TM Total Knee System", Brochure No. 81-038-5230-1004/15MB, Zimmer USA, Inc., Warsaw, IN, 26 pages (1981).
"Knee Replacement Using the Insall/Burstein Total Condylar Knee System", Brochure No. 81-038-22-6-1020/15MZ, Zimmer, Inc., Warsaw IN, 22 pages (1981).
"Insall/Burstein TM Total Knee System with I/B/F TM Total Knee Instrumentation", Brochure No. 84-038-5230-0172 Rev. 2/5MB, Zimmer, Inc., Warsaw, IN, 36 pages (1981).
"R.M.C. TM Total Knee System—Technique", Brochure No. 3246 Rev. 9-79, Richards Mfg. Co., Memphis, TN, 35 pages (1979).

Primary Examiner—C. Fred Rosenbaum
Assistant Examiner—C. W. Shedd
Attorney, Agent, or Firm—Susan M. Cornwall

[57] ABSTRACT

The present invention relates to a surgical apparatus for providing an accurately placed recess in a distal femoral surface for the intercondylar stabilizing housing of a posterior-stabilized knee implant prosthesis which apparatus comprises (a) a template having (1) a bottom surface which is adapted to be placed in an aligning relationship with the flat surface of a distal femur which has been partially shaped to receive the femoral component of a posterior-stabilized knee implant prosthesis and (2) a U-shaped slot passing through the template where the slot is of substantially the same size and shape as the outer periphery of the intercondylar stabilizing housing present on the femoral component to be implanted and (b) a drilling means, preferably in the form of an end-mill cutter, having a stop means thereon and the drilling means closely engages the sides of the U-shaped slot in the template so that the drilling means can be passed through the U-shaped slot until the stop means contacts a surface of the guide and is then drawn along the slot to create a precisely shaped and aligned recess in the femur for receipt of the intercondylar stabilizing housing. In a more preferred embodiment, the template is composed of a drilling means guide which fits over a femoral trial prosthesis which is used for trial reductions after the drill guide is used and removed.

7 Claims, 21 Drawing Figures

FEMORAL SURFACE SHAPING APPARATUS FOR POSTERIOR-STABILIZED KNEE IMPLANTS

BACKGROUND OF THE INVENTION

This invention relates to a surgical apparatus comprising a template and a cooperating drilling means for completing the preparation of a distal femoral surface to accurately receive a femoral component of a posterior-stabilized knee implant prosthesis.

A posterior-stabilized knee prosthesis is indicated for a patient who suffers from an unstable, painful knee joint where the instability is caused by the lack of or inadequacy of the posterior cruciate ligaments. The posterior-stabilized knee implant prosthesis consists of a tibial component with a stabilizing post protruding from the superior surface of the tibial component, a femoral component with an intercondylar stabilizing housing to accept the stabilizing post which provides the stability which the patient's knee joint lacks and typically includes a patella component. The housing on the femoral component is intended to fit snugly within the cancellous bone of the distal femur. For optimum results after implantation, it is very important that the femoral and tibial components of the prosthesis be properly aligned relative to the femur and tibia, respectively, during implantation of the components.

Several two-component posterior-stabilized knee prostheses are presently commercially available. See, for example the HOWMEDICA ® KINEMATIC ™ Stabilizer Prosthesis from Howmedica, Inc. of Rutherford, N.J. which is described in Brochure No. ST 3210-1 2/81 15M B dated February, 1981 entitled "The Howmedica ® Kinematic ™ Knee System—Howmedica ® Surgical Techniques". To implant the femoral component of this prosthesis, page 9 of the Brochure indicates that after the distal femoral surface is prepared to produce flat distal femoral surfaces, the KINEMATIC Stabilizer Prosthesis trial femoral component is placed on the distal femur. Using methylene blue dye, the outline of the intercondylar stabilizing housing is marked on the flat surface of the distal femur. A recess for the housing is then made by removing bone from within the marked area using an osteotome. The surgeon is only guided by the blue marking on the flat surface of the distal femur and must try to keep within that area. The surgeon must also estimate the depth to which bone must be removed to enable the housing to be completely received within the recess.

The INSALL/BURSTEIN ™ Total Knee System from Zimmer USA, Inc. of Warsaw, Ind. is described in Brochure No. 81-038-5230-1004/15MB dated 1981 and entitled "Insall-Burstein ™ Total Knee System". Page 22 of the brochure describes a Femoral Trimmer instrument (No. 5230-30) which is mounted on the femur to accomplish resection of the anterior and posterior condyles and also contains vertical slots to indicate cuts to the distal femur to create the recess for the trough (stabilizing housing) of the femoral component. Page 24 of that Brochure shows an alignment guide set which contains spacer guides having handles which are used to mark the "approximate" width of the intercondylar groove of the femoral component. Page 25 of that Brochure shows an Intercondylar Trough Gauge (Nos. 5230-40 through 5230-43 for various widths) to provide a means of checking the resected distal femur to assure that the intercondylar notch has been correctly resected to a depth of 20 mm. That page states that the surgeon uses the sizer to make a "visual determination of which area may be improperly resected" if the surgeon observes that the sizer does not fit flush against the resected distal femur. Thus, the surgeon is required to possibly repeatedly resect the bone away from the femur until a proper size recess is created in the distal femur.

Page 17 of Brochure No. 81-038-226-1020/15MZ dated 1981 and entitled "Knee Replacement Using Insall/Burstein Total Condylar Knee System" also from Zimmer USA, Inc. further describes the manner in which a femoral trimmer of the type described in the Howmedica Brochure above is used to create a shallow vertical trough 8 mm deep in the center of the distal femur. Page 17 notes that while the femoral trimmer may be used to determine the width of the notch to be cut to receive the stabilizer housing, the "hole in the femoral shaft may no longer be in the correct position to reinsert the instrument" (due to the cuts made to shape the femur). For this reason, page 17 recommends that a simpler method is to use an alignment guide handle to place marks on the femur and "the marks are subsequently cut to allow for the trough . . . ." It is still up to the surgeon to saw the distal femur to the proper depth and width using the marks as a guide. Even use of the alignment guide only provides cuts which define the width of the recess needed for the housing; the surgeon must resect the bone to the appropriate depth using a saw or an osteotome along with the Intercondylar Trough Gauge to confirm that the appropriate depth has been reached. In another Zimmer USA, Inc. Brochure (No. 84-038-5230-0172 Rev. 2/5MB dated 1981) entitled "Insall/Burstein ™ Total Knee System With I/B/F ™ Total Knee Instrumentation" on pages 31 and 33, still another method is described which employs a template which is used to create a trough across the entire distal femoral surface using a saw and an osteotome.

There still appears to be a need for a surgical apparatus which will accurately and simply provide a snugly-fitting and accurately-aligned recess for the intercondylar stabilizing housing of the femoral component of a posterior-stabilized knee implant prosthesis.

SUMMARY OF THE INVENTION

One object of the present invention is to provide a surgical apparatus which will enable a surgeon to simply and accurately complete the precise shaping of a distal femoral surface for receipt of the intercondylar stabilizing housing of the femoral component of a posterior-stabilized knee implant prosthesis. Another object of the present invention is to minimize the number of instruments needed by a surgeon to accomplish the implantation of such a femoral component prosthesis.

A further object of the present invention is to provide an apparatus which not only serves to guide a surgeon in completing the shaping of the distal femoral surface, but also provides a femoral trial prosthesis which can be used for trial reduction of the tibial component of the prosthesis. This reduces the number of times which a prosthesis is placed in contact with the newly shaped distal femoral surface. This is an advantage in that the prosthesis to be implanted will be in contact with a precisely shaped surface and will have the opportunity to optimally bond with the distal femoral surface. This is significant where a cementless prosthesis which bonds by bone ingrowth into the porous bone-contacting surface of the prosthesis is to be affixed to the femur. Another object of the present invention is to shape the distal femur in a precise manner to receive the implantable femoral component while at the same time retaining as much of the bone surrounding the component as possible to thereby provide a tightly fitting implantable femoral component.

These and other objects of the present invention are provided by an apparatus which comprises (a) a template having (1) a bottom surface which is adapted to be placed in an aligning relationship with the flat surface of a distal femur which has been partially shaped and marked to receive the above femoral component and (2) a U-shaped slot passing through the template where the slot is of substantially the same size and shape as the outer periphery of the intercondylar stabilizing housing present on the femoral component to be implanted and (b) a drilling means, preferably in the form of an end-mill cutter, having a stop means thereon and the drilling means closely engages the sides of the U-shaped slot in the template so that the drilling means can be passed through the U-shaped slot until the stop means contacts a surface of the guide and is then drawn along the slot to create a precisely shaped and aligned recess in the femur for receipt of the intercondylar stabilizing housing. In a more preferred embodiment, the template comprises a femoral trial component (which does not contain an intercondylar stabilizing housing) which is placed on the flat shaped surface of the distal femur followed by a drilling means guide which conforms to and fits over the condylar surface of the trial component so that the recess for the intercondylar stabilizing housing may be created and the drilling means guide is then removed to enable the surgeon to accomplish trial reduction of the implant prosthesis without having to remove the trial component from the shaped distal femoral surface.

BRIEF DESCRIPTION OF THE DRAWINGS

The above and other objects, features, and advantages of the present invention will become apparent to those skilled in the art upon an examination of the following description and drawings which are illustrative of the present invention.

In the Drawings.

DETAILED DESCRIPTION OF THE INVENTION

Figure 1:
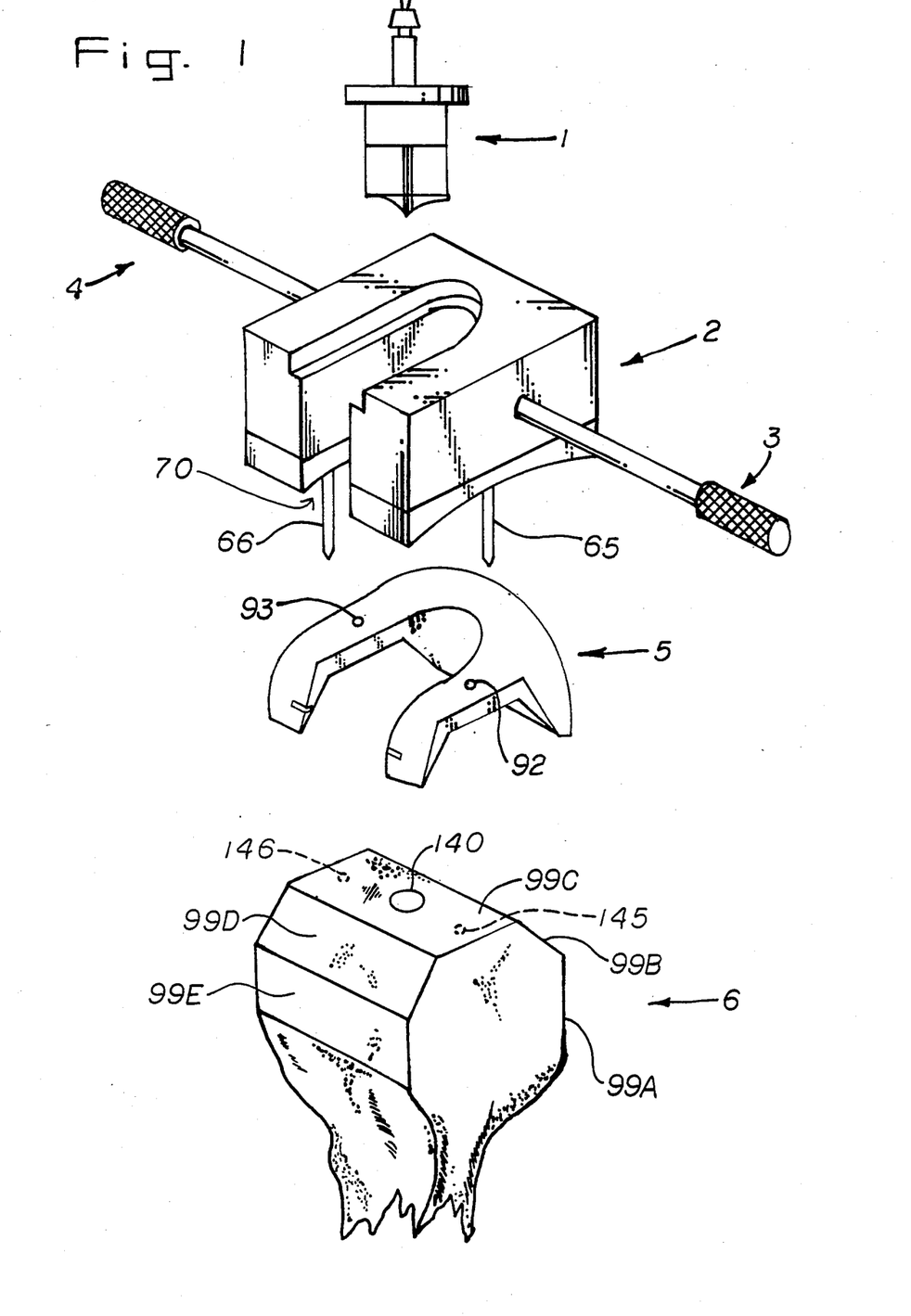
FIG. 1 is an exploded perspective view of the preferred embodiment of the apparatus of the present invention shown above a partially shaped distal femur 6 prior to creating a recess for the receipt of an intercondylar stabilizing housing.

Referring to the Drawings, FIG. 1 depicts the preferred embodiment of the apparatus of the present invention prior to creating a recess in distal femur 6 which comprises end-mill cutter 1 which closely fits into a U-shaped slot 70 in drill means guide 2 which has opposed handles 3 and 4 for holding guide 2 firmly in position on femoral trial component 5 which, in turn, is placed over a partially shaped distal femur 6 where the femur has been shaped to receive trial component 5 in proper alignment with the distal femur.

Figure 2:
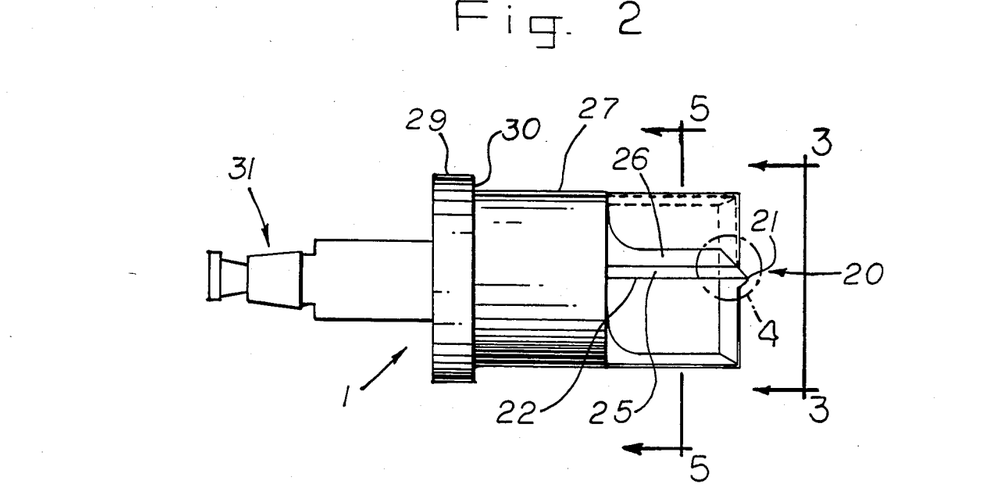
FIG. 2 is a side view of end-mill cutter 1.
Figure 3:
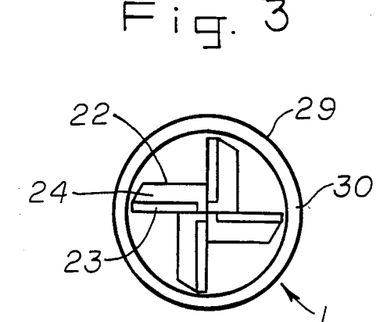
FIG. 3 is a view of FIG. 2 taken from the bottom.
Figure 4:
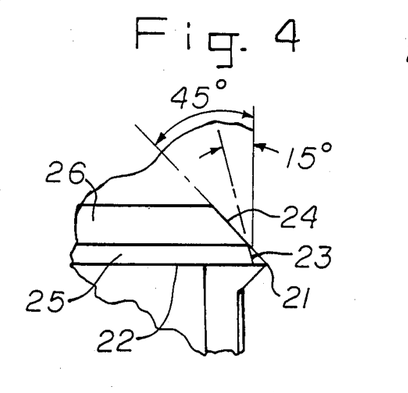
FIG. 4 is an elevational view of area 4 of FIG. 2.
Figure 5:
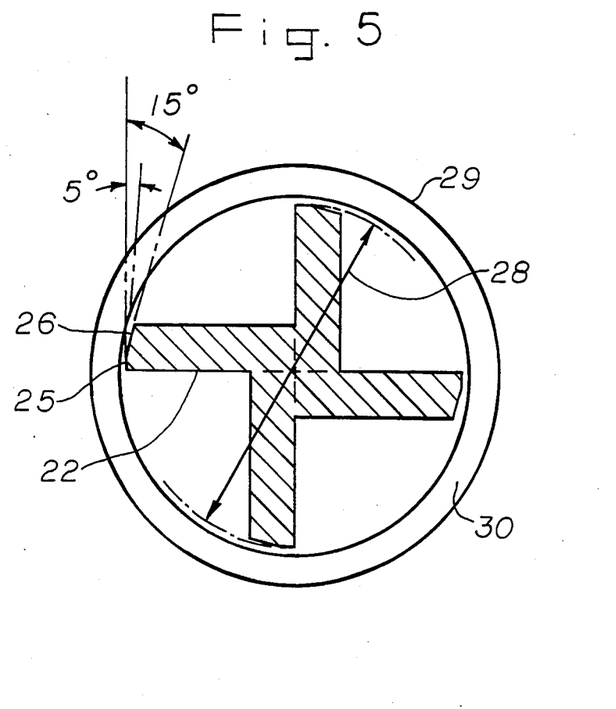
FIG. 5 is a cross-sectional view of FIG. 2 taken along section lines 5—5 in the direction of the arrows.

FIG. 2 shows metal end-mill cutter 1 having an end cutting edge 20 having a centering point 21 and four cutter blades, one of which is referred to by reference numeral 22. FIGS. 3 and 4 show further details of end cutting edge 20 showing the arrangement of the cutter blades. FIG. 4 shows the detail of area 4 in FIG. 2 and shows the preferred end cutting blade angle of 15 degrees on face 23 and the preferred end cutting blade relief angle of 45 degrees on face 24. End cutting blade 22 contains face 25 which is shown in FIG. 5 as being set at the preferred cutting angle of 5 degrees and face 26 which is set at the preferred cutting blade relief angle of 15 degrees. Each of the other three cutting blades has the same configuration for the end and side cutting portions of each blade as does blade 22. Four cutter blades are preferred although a three cutting blade configuration can also be used with good results.

The cutting blades are concentrically fixed to a smooth cylinder 27 in such a manner that the outside diameter 28 of a circle swept by the rotating blades is slightly smaller than the outside diameter of cylinder 27 and matches the width of the recess to be placed in femur 6. The outside diameter of cylinder is adapted to closely conform with the width of U-shaped slot 70 in drilling means guide 2 to guide cutter 1 and is of a sufficient length to prevent the side cutting blades of cutter 1 from contacting the sides of U-shaped slot 70 and possibly placing metal shavings in the femur.

The upper end of cylinder 27 is fixed to a larger diameter cylindrical stop means 29 having a lower surface 30 which is intended to contact surface 73 of U-shaped slot 70 to stop cutter 1 from going any further into femur 6 and thus limits the depth of the recess created in femur 6. A conventional standard "Hudson" shank is concentrically affixed to stop means 29 to provide a means by which cutter 1 can be engaged with the chuck of a power-driven drill.

Figure 6:
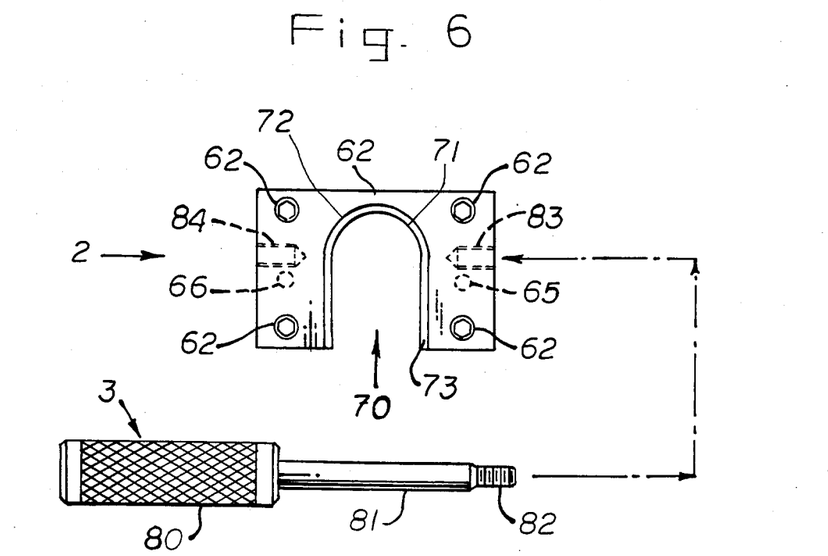
FIG. 6 is a plan view of drilling means guide 2 further showing the placement of handle 3.
Figure 7:
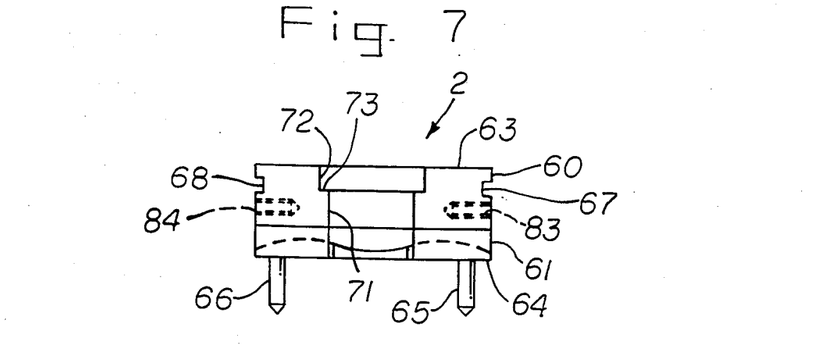
FIG. 7 is a side view of FIG. 6 from the direction of the opening of U-shaped slot 70.
Figure 8:
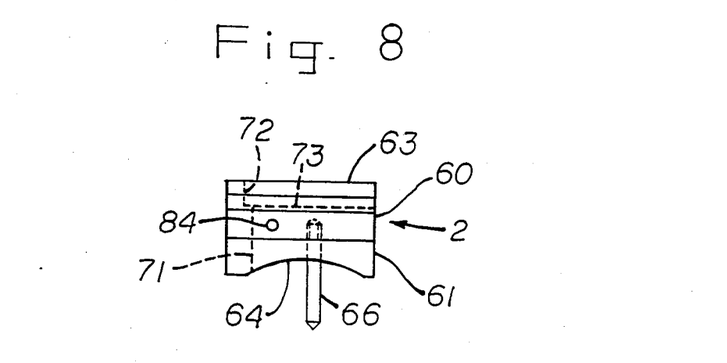
FIG. 8 is a side view of the left side of FIG. 7.

Referring to FIGS. 6-8, drill means guide 2 is shown in its preferred form which is a metal upper component 60 and a plastic lower component 61 joined together by some means such as screws 62 which are countersunk through upper surface 63 of component 60 and are fastened into component 61. The lower surface 64 of component 61 conforms to the distal condylar surfaces (i.e., the surfaces which contact the corresponding portion of surface 174 of tibial component 171 of FIG. 17) of condyles 90 and 91 shown in FIGS. 9A-9C and contains two projecting pegs 65 and 66 which are intended to pass through holes 92 and 93 in trial component 5 to bring guide 2 into proper alignment with component 5. Pegs 65 and 66 are fastened within component 60 as shown in outline form in FIGS. 6 and 8. Component 61 is preferably made of a rigid polymeric material such as an acetal resin sold under the trademark "DELRIN" by the E. I. duPont de Nemours, Inc. of Wilmington, Del. to minimize deformation or scratching of the distal condylar surfaces of condyles 90 and 91 of trial component 5 when guide 2 is fixed to and removed from trial component 5 and thereby enable trial component 5 to be used in trial reduction procedures.

Guide 2 contains U-shaped slot 70 where the rounded portion of slot 70 is located centrally and U-shaped slot 70 opens in the direction of the posterior of the femur in which a recess is to be created. The wall 71 forming slot 70 runs parallel to the central long axis of femur 6 when guide 2 is mounted on trial component 5 and femur 6 so that cutter 1 is guided by wall 71 in a manner which is parallel to that axis. Wall 72 which is wider than wall 71 parallels the periphery of wall 71 and is at least as wide as the diameter of stop 29. Surface 73 provides a contact surface for surface 30 of cutter 1 which stops the travel of cutter 1 into the femur. If desired, wall 71 could be extended through to surface 62 and surface 30 could simply contact surface 62 to stop the travel of cutter 1.

Component 60 is also provided with notches 67 and 68 which permit an extractor instrument (not shown) of a conventional type commonly used for removal of a femoral trial component. The extractor instrument has the appearance of a wide-jaw pair of pliers which contains an extension at the edge of the jaws which fits into each notch 67 and 68 when the extractor instrument jaws are closed to permit the surgeon to remove component 60 from the distal femur without damaging the newly shaped distal femur. An example of such an instrument is the Femoral Trial Extractor Catalog No. 1610-0052 sold by Dow Corning Wright Corporation of Arlington, Tenn.

FIG. 6 shows the manner in which metal handle 3 which is composed of a knurled gripping portion 80 fixed to rod 81 having threaded male end 82 can be screwed into female threaded hole 83 in component 60 and is shown assembled in FIG. 1. Handle 4 has the same configuration as handle 3 and is screwed into threaded hole 84 in component 60.

Figure 9A:
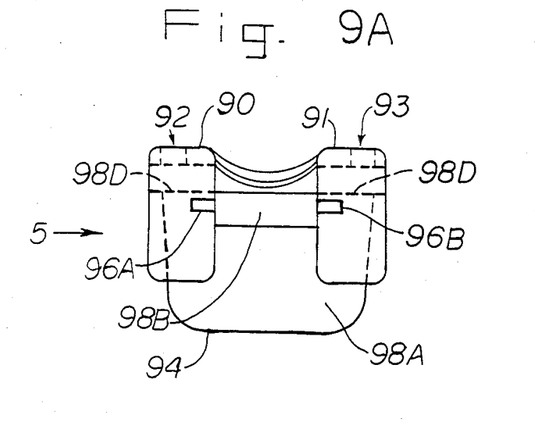
FIGS. 9A, 9B and 9C show rear (posterior), side and front (anterior) views, respectively, of femoral trial component 5.
Figure 9B:
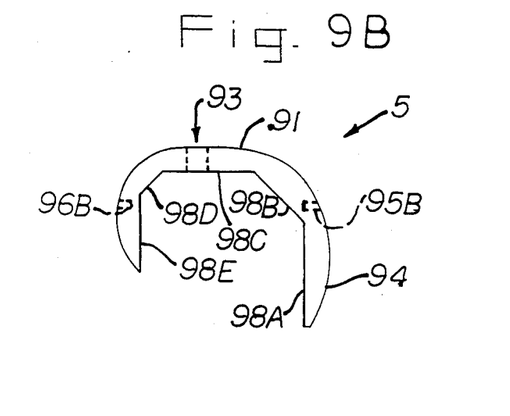
Figures 9C, 10, 11:
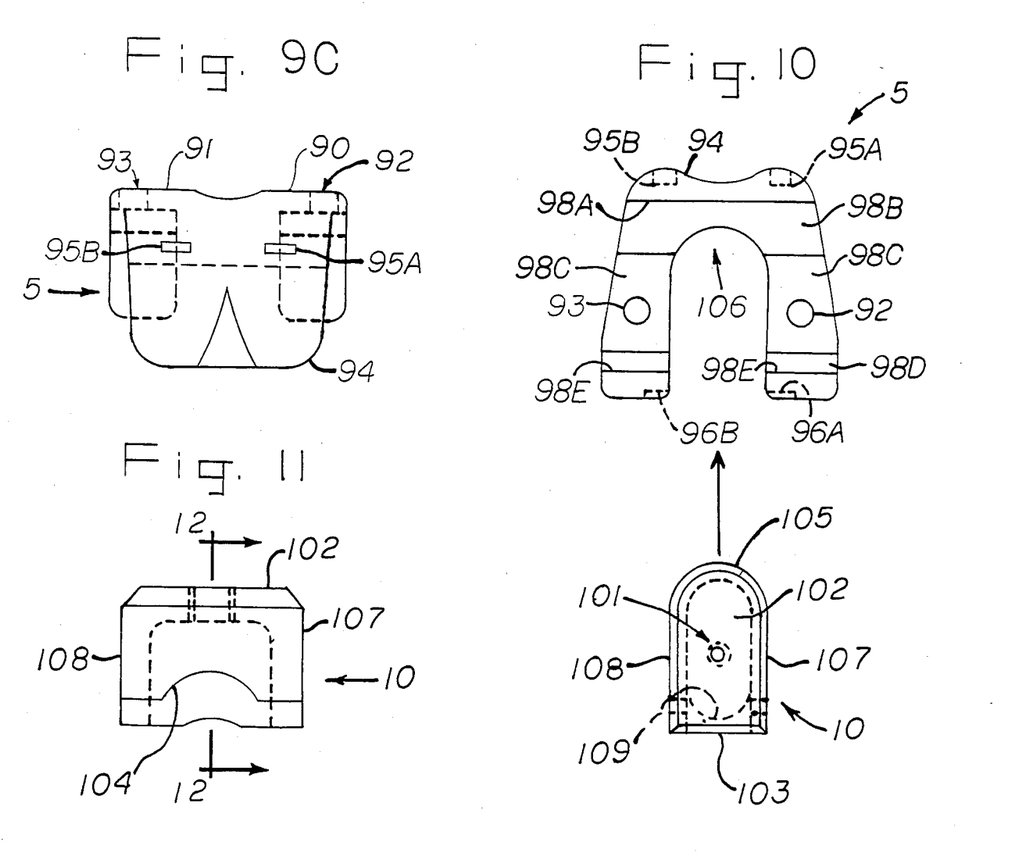
FIG. 10 is a plan view of trial component 5 showing the manner in which trial intercondylar stabilizing housing 10 can be placed in trial component 5.
FIG. 11 is an end (posterior) view of trial intercondylar stabilizing housing 10.

FIGS. 9A, 9B AND 9C show metal trial femoral component 5 which also serves to hold guide 2 in proper alignment with respect to the distal femoral surface to be shaped. Trial component 5 will be described with respect to a prosthesis which can be used for either knee. Thus, trial component 5 is composed of condyles 90 and 91 where the distal condylar surface of each condyle is selected to conform with the upper surface of the tibial component and thereby mimic the manner in which the human knee functions after the components are implanted (see FIG. 17). Guide holes 92 and 93 pass through condyles 90 and 92, respectively, and have an inside diameter which is only slightly larger than the outside diameter of pegs 65 and 66 which are intended to pass through holes 92 and 93 and extend into femur 6 to secure trial component 5 and guide 2 to the end of shaped distal femur 6. The outside diameter of pegs 65 and 66 is selected to be slightly smaller in diameter than the diameter of pegs 132 and 133 of femoral component 13 shown in FIGS. 13A and 13C which will be affixed to the distal femur 6 after the distal femoral surface is shaped to insure that implantable component 13 will tightly fit the distal femur 6.

Condyles 90 and 91 are joined together by anterior patellar flange 94 which contains notches 95A and 95B. Condyles 90 and 91 similarly contain notches 96A and 96B, respectively. Notches 95A, 95B, 96A and 96B serve the same purpose as notches 67 and 68 and permit the surgeon to remove trial component 5 from the distal femur using an extractor instrument with appropriately shaped jaws for gripping the notches.

Proximal surfaces 98A, 98B, 98C, 98D, and 98E of trial component 5 are intended to contact shaped surfaces 99A, 99B, 99C, 99D and 99E, respectively, of femur 6 and and have the same configuration and dimensions as the corresponding femur-contacting surfaces of implantable component 13.

Figure 12:
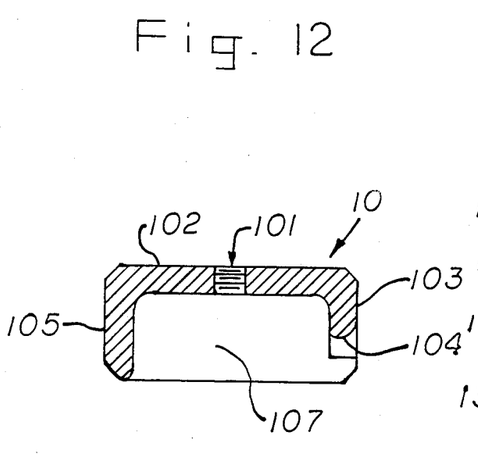
FIG. 12 is a cross-sectional view along section lines 12—12 of FIG. 11 in the direction of the arrows.

Referring to FIGS. 10-12, the detail of trial intercondylar stabilizing housing 10 and the manner in which it is inserted in trial component 5 is shown. Rectangular housing 10 has the same size and shape as housing 1310 found in implantable component 13 with the exception that a threaded hole 101 passing through top surface 102 is included so that a threaded rod (not shown) connected to a handle may be screwed into hole 101 and used to remove housing 10 from the recess in the femur as will be described below. Housing 10 fits between condyles 90 and 91 in the same place where housing 1310 in permanently implantable component 13 is positioned and has interior dimensions which, for example referring to FIG. 17, enable stabilizing post 172 on tibial component 171 to stay within the interior of housing 1310 of implantable component 13. The posterior wall 103 of trial housing 10 has a raised opening 104 of the same size as opening 1314 in housing 1310 to ultimately permit implantable component 13 to slide along the upper surface of component 171 when the knee is bent up to the point where stabilizing post 172 on component 171 contacts the edge of opening 1314 to permit normal flexion of the knee. Rounded anterior wall 105 of housing 10 fits within rounded portion 106 of the U-shaped opening formed by the space between condyles 90 and 91. The width of side walls 107 and 108 of housing 10 is selected to be equal to that of the housing 1310 and the space between condyles 90 and 91 is made large enough to permit housing 10 to fit closely within that space. The shape of the interior of housing 10 is shown in FIG. 10 in outline form by reference numeral 109.

Figure 13A:
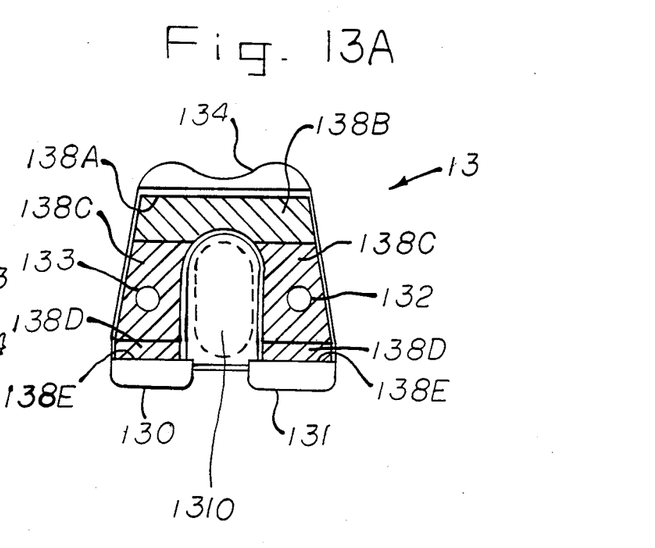
FIGS. 13A, 13B and 13C are plan, rear (posterior), and side views, respectively, of implantable femoral component 13 having intercondylar stabilizing housing 1310.
Figure 13B:
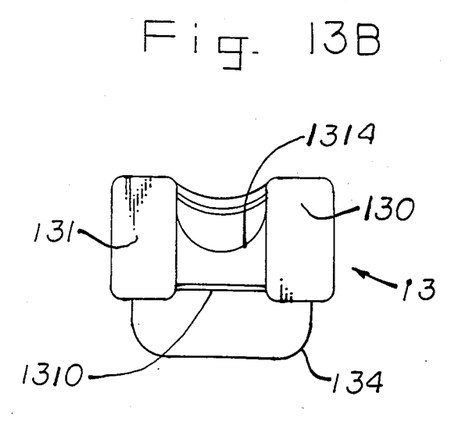
Figure 13C:
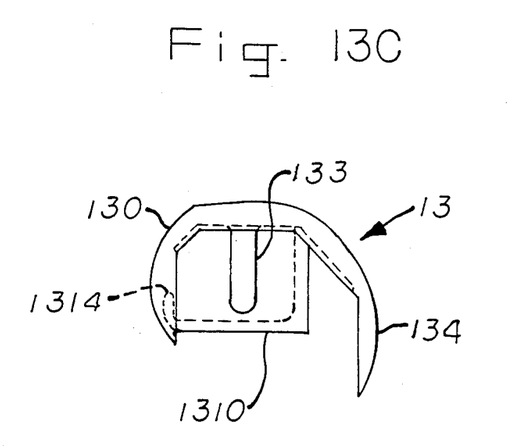

FIGS. 13A-13C show implantable femoral component 13 for the right femur having intercondylar stabilizing housing 1310 permanently located between condyle 130 and condyle 131. Condyles 130 and 131 are joined together by patellar flange 134 as well as the walls of housing 1310. Surfaces 138B, 138C, and 138D are provided with a bone ingrowth material coating such as a porous metal coating as well as mounting pegs 132 and 133 to accomplish fixation of implantable component 13 to the distal femur. Housing 1310 has posterior raised opening 1314 which is of the same size and shape as opening 104 in trial housing 10. Thus, when housing 10 is placed within trial component 5, it has the same geometrical configuration as does implantable component 13 (with the exception of pegs 132 and 133) and can therefore serve as a trial component for the trial reduction of the prosthesis 17 which is to be implanted.

The above described cutter 1, upper component 60 of guide 2, and trial component 5 are all preferably manufactured from a suitable surgical grade of stainless steel or other metal commonly employed by those skilled in the art to construct surgical tools for use in contact with the body. Lower component 61 is preferably made from a plastic for the reasons described above, but could be made of a metal of the above type and, if desired, the entire guide 2 could be of the above type of metal. The exact composition of the metal and plastic used to construct the above forms no part of the present invention; other metals and plastics suitable for use within the body and for the intended uses of the cutter, guides and components may be used without altering the nature of the invention.

The manner in which the apparatus of the present invention may be used will now be described. The first objective is to shape the distal femur to produce at least one flat distal femoral surface. A number of conventional surgical procedures are known to surgeons which will enable the surgeon to reach the point where the femur has been partially shaped to the extent that the surgeon is ready to create a recess for the intercondylar stabilizing housing of the posterior-stabilized knee prosthesis. It is at this point in the surgical procedure that the apparatus of the present invention comes into use. Various posterior-stabilized knee prosthesis manufacturers publish surgical procedures for use by surgeons in implanting their prostheses as can be seen from an examination of the surgical procedures for the Howmedica, Inc., and Zimmer USA, Inc. products identified above. For the purposes of the present invention, the surgical procedures employed to create a shaped distal femur described using the "Method and Apparatus For Shaping A Distal Femoral Surface" described in U.S. Pat. No. 4,474,177 to Leo A. Whiteside (issued Oct. 2, 1985) are preferably employed. The Whiteside Patent method is hereby incorporated by reference to teach one method by which the distal femur may be shaped prior to using the apparatus of the present invention to complete the shaping of the distal femur to receive a posterior-stabilized knee implant prosthesis.

Referring to FIGS. 1 and 14–16, femur 6 is shown stripped of all other anatomical structures normally present for purposes of clarity. Femur 6 is shown in FIG. 1 as having been shaped to receive trial component 5 in accordance with the method of the Whiteside '177 Patent so that the femur contains a hole 140 left when the intramedullary alignment guide taught in the '177 Patent was removed. An anterior-posterior cutting guide, a distal femoral condyle cutting guide, a plateau planer, and a bevel cutting guide were attached to that intramedullary alignment guide and were employed in accordance with that method to create surfaces 99A–99E on femur 6 which correspond to the surfaces 138A–138E of implant component 13. Holes 145 and 146 (shown as dotted lines in FIG. 1) are created by pegs 65 and 66. Holes 145 and 146 thus ultimately serve as alignment marks on flat distal surface 99C for proper alignment of implant component 13 on distal femur 6.

Figure 14:
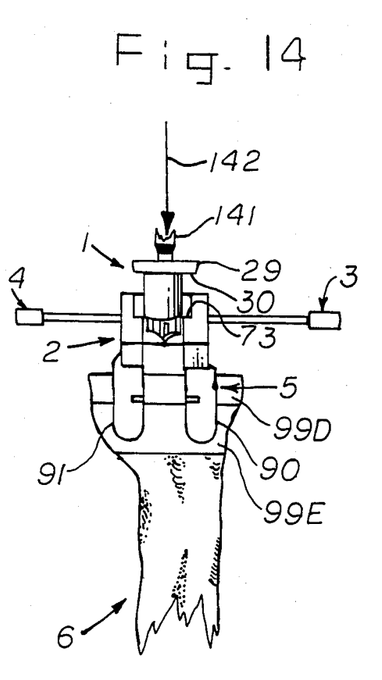
FIG. 14 is a rear view of guide 2 mounted on trial component 5 with power-driven cutter 1 being started along surface 73 to begin the formation of a recess for housing 10 in femur 6.

Trial component 5 is centered on shaped distal femur 6 over surfaces 99A–99E. Guide 2 with handles 3 and 4 is placed over trial component 5. Pegs 65 and 66 are then passed through holes 92 and 93, respectively, and thereafter driven into femur 6 to create holes 145 and 146 (which are shown as dotted lines in FIG. 1), respectively, to mount guide 2 over trial component 5. Thus, the U-shaped slot 70 is placed in the proper position to be used to create a recess for housing 10. Handles 3 and 4 are held by a surgeon's assistant to secure the guide 2 on distal femur 6 while the recess is created. FIG. 14 shows the assembled apparatus.

End-mill cutter 1 is secured in chuck 141 of a power-driven drill, cutter 1 is placed against the rounded portion of slot 70, and the drill motor is started. Cutter 1 is pushed into femur 6 in the direction of arrow 142 using wall 71 as a guide until surface 30 of stop 29 contacts surface 73 of guide 2 and stops the progress of cutter 1 into femur 6 in the direction of arrow 142. In designing the drilling means guide and cutter, the distance between surface 73 and the bottom of the recess to be created is used to determine the distance between surface 30 and the cutting edge of cutter blade 22 (point 21 is not included) that is required so that the depth of the recess matches the depth in the femur 6 needed to insert housing 10 after the cutter is allowed to bore into the femur up to the stop means.

Figure 15:
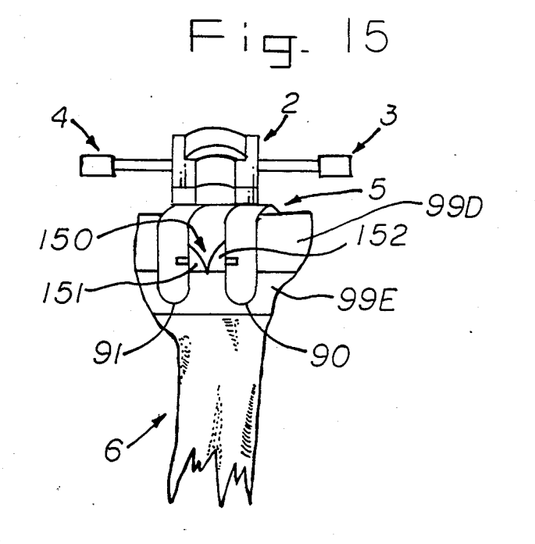
FIG. 15 is a perspective view of femur 6 after cutter 1 has created a substantial portion of recess 150.

When surface 30 of end-mill cutter 1 contacts surface 73, recess 150—which is shown in FIG. 15 with a small amount of bone 151 and 152—is created. End-mill cutter 1 can be moved posteriorly to remove bone 151 and 152 or, more preferably, bone 151 and 152 can be removed with a saw using the side walls of slot 70 of guide 2 as saw guides to complete the formation of recess 150 for trial housing 10 (and, ultimately, for implant housing 1310 of implant component 13).

Figure 16:
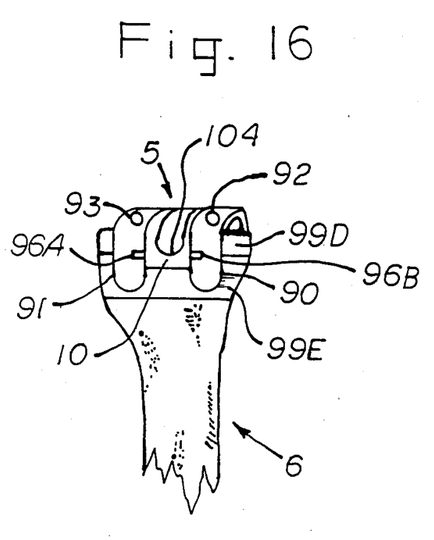
FIG. 16 is a perspective view of femur 6 with housing 10 placed in recess 150.

FIG. 16 shows trial component 5 with trial housing 10 in place in recess 150. Guide 2 has been removed and the distal femur is now ready for trial reduction to test range of motion and stability of the knee in accordance with conventional surgical techniques which are well known to those skilled in the art.

When the trial reduction is completed, a threaded rod (not shown) is inserted into threaded hole 101 of trial housing 10 and trial housing 10 is removed from recess 150. An extractor instrument (not shown) is used to grasp notches 95A, 95B, 96A and 96B and remove trial component 5 from shaped distal femur 6.

Figure 17:
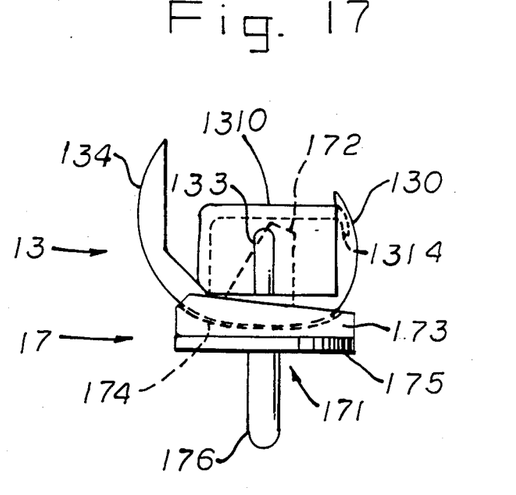
FIG. 17 is a side view of a posterior-stabilized knee implant prosthesis 17 showing, in outline form, the manner in which implantable femoral component 13 and tibial component 171 fit together.

After implantable tibial component 171 is fixed to the tibia, implantable component 13 is then tightly fixed to shaped distal femoral surfaces 99A–99E. Surfaces 99A–99E have only been contacted once by trial component 5 and housing 10 and therefore an optimum fit for implantable component 13 is obtained. After the implantable femoral and tibial components have been inserted, the procedure may be completed and the wound closed in the usual manner employed for posterior-stabilized knee implant prostheses.

FIG. 17 shows the relationship between femoral component 13 and a corresponding tibial component shown in the form of tibial component 171 having stabilizing post 172 set in the central portion of plastic (e.g., ultra-high molecular weight polyethylene) insert 173. Insert 173 has an upper surface 174 which contacts the distal surface of condyles 130 and 131 of implant prosthesis 13 to enable condyles 130 and 131 to articulate over surface 174 when the patient's knee flexes. Insert 173 is contained within metal tray 175 which contains fixation post 176 to provide a means for attaching tibial component 171 to a shaped tibial plateau.

It will be readily apparent to those skilled in the art that guide 2 and trial component 5 could be combined into one single cutting means template as long as there is provided a means for placing the template on at least one shaped flat distal femoral surface so that the template is properly aligned with respect to the femur and the implant to be placed on that distal femur. This is a less preferable, but useful, configuration since the recess can be accurately created, but a separate trial component prosthesis (or the implantable femoral component itself) must then be additionally used for trial reduction.

Other modifications of the apparatus of the present invention will become apparent to those skilled in the art from an examination of the above specification and drawings. Therefore, other variations of the present invention may be made which fall within the scope of the following claims even though such variations were not specifically discussed above.

What is claimed is:

1. An apparatus for completing the preparation of a distal femur which has been partially shaped to receive a femoral component of a posterior- stabilized knee implant prosthesis having an intercondylar stabilizing housing wherein said femur has been shaped to contain a flat distal femoral surface, said apparatus comprising, in combination:
   (a) a template having a bottom adapted to be placed on said flat distal femoral surface such that a slot having a U-shaped perimeter and being of substantially the same size and shape as the stabilizing housing passing through said template is situated over that portion of said femur which is to be removed to provide a shaped recess in said distal femur for the receipt of the stabilizing housing of said femoral component, wherein the open-ended portion of said slot of said template opens in the direction of the posterior portion of the femur when the template is placed on the femur, said slot being adapted to cooperte with and closely engage the sides of
   (b) a drilling means, said template having a sufficient thickness between the bottom and the top of said template to thereby direct said drilling means into said femur, relative to said flat distal femoral surface, to create at least a major portion of said recess, there being a stop means present on said drilling means to control the depth to which said drilling means enters said femur so that the depth of the recess created matches the height of the stabilizing housing of the implant to be fixed to said distal femur.

2. The apparatus of claim 1 wherein said drilling means comprises an end-mill cutter having cutting surfaces at the lower end of the cutter and along the bone contacting portion of the sides of the cutter parallel to the central long axis of the cutter to accomplish side-cutting of said femur.

3. The apparatus of claim 1 wherein said template comprises the combination of a femoral trial implant prosthesis having two spaced-apart condyles and an opening between said condyles slightly larger than the width of the stabilizing housing and the trial implant prosthesis has an upper surface adapted to fit over said prepared surface and an articulating surface having the same configuration as the condylar portion of the posterior-stabilized knee implant prosthesis to be implanted and is further adapted to receive the lower end of a drilling means guide containing said in such a manner that the slot is aligned relative to the flat distal femoral surface to accomplish creation of said recess.

4. The apparatus of claim 3 wherein said drilling means guide further contains two handles extending away from opposite sides of said drilling guide which handles are perpendicular to the central long axis of said slot and are perpendicular to the sides of said slot.

5. The apparatus of claim 3 wherein the lower portion of said drilling means guide is made of a rigid polymeric material to prevent scratching of said lower surface of said femoral trial implant prosthesis.

6. The apparatus of claim 3 where the apparatus further includes a separate trial intercondylar stabilizing housing of substantially the same dimension as the intercondylar stabilizing housing present on the femoral component to be implanted, said trial intercondylar stabilizing housing fitting between the condyles of the trial implant prosthesis.

7. The apparatus of claim 1 wherein said template further contains two handles extending away from opposite sides of said template which are perpendicular to the central long axis of said U-shaped slot and are perpendicular to the sides of said U-shaped slot.

* * * * *